Sept. 18, 1973 R. H. McCOLLEY Plant Pat. 3,397
DISTINCT VARIETY OF PHILODENDRON PLANT
Filed April 10, 1972
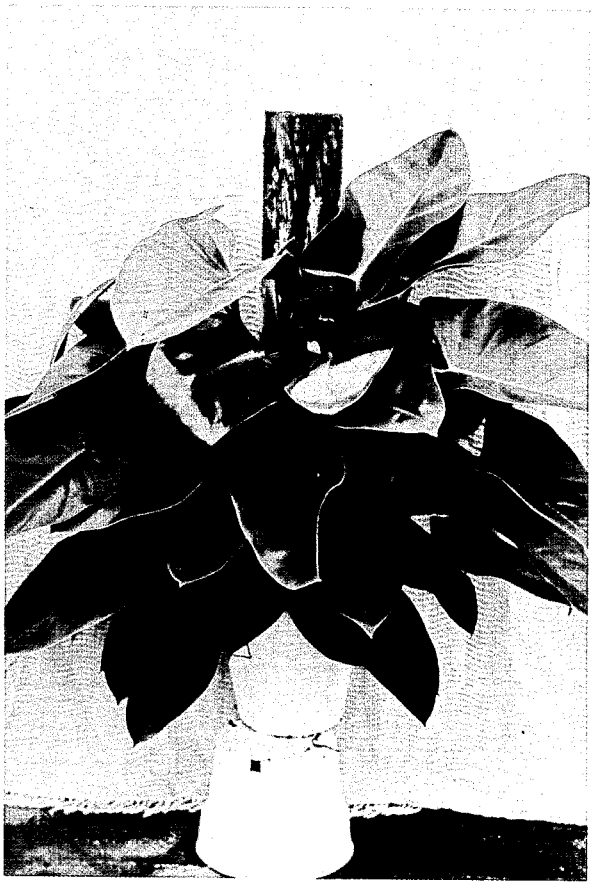

United States Patent Office

Plant Pat. 3,397
Patented Sept. 18, 1973

3,397

DISTINCT VARIETY OF PHILODENDRON PLANT

Robert H. McColley, P.O. Box 17126,
Orlando, Fla. 32810

Filed Apr. 10, 1972, Ser. No. 242,845
Int. Cl. A01h 5/00
U.S. Cl. Plt.—88 1 Claim

ABSTRACT OF THE DISCLOSURE

The disclosure hereof is a Philodendron plant having characteristics of particular density of growth, with wide leaves, short petioles and close internodes, the durability of the plant without watering at long intervals is an important aspect, the leaves being tough and leathery with very shiny appearance, even more so than usual Philodendrons.

DESCRIPTION OF THE INVENTION

My present invention comprises a new and distinct variety of Philodendron plant which is the result of crossing an unnamed species which I have used for breeding work for many years with an unnamed seedling whose parentage includes *Philodendron hastatum, Philodendron erubescens, Philodendron wendlandii* and *Philodendron imbe.*

While my new variety has some of the characteristics of certain of the species and hybrids, in most aspects it is substantially different. The hybrid of my own production, although not patented, is a Philodendron known in the trade as Emerald Queen which is an industry standard and accounts for a substantial proportion of the green, entire leaved, green stemmed poles produced in the trade currently.

The variety of my Plant Patent No. 3,081 has certain of the characteristics, but my new variety is, in any event, distinguishable from that of the plant patent heretofore named.

One of the problems with other species of *Philodendrons* such as *brenesii, cordatum* (true) and *ficutissum,* are all related but do not have the keeping qualities and overall form nor the commercial value of the instant invention.

I have therefore primarily improved over the earlier variety of industry standard known as Emerald Queen, since my new variety has leaves which are at least 20% wider than my former variety, and 25% thicker with .015 inch thick leaves on my new variety and thinner leaves on the earlier variety being used as a comparison.

Another novel aspect of my new variety is the rubber-like texture and high natural gloss which is evident from comparing the leaves of the respective plants. This high natural gloss is emphasized by the more dense growth of my new variety with twice as many leaves at virtually any height as compared to the earlier variety referred to.

A further distinguishing aspect is the fact that the petioles of my new variety are 20% shorter than and 20% thicker than those of the industry standard Emerald Queen.

Other important characteristics of my new variety which distinguish it from the earlier industry standard, are the fact that the rate of height development under greenhouse conditions is substantially less than that of the earlier variety, and in fact when placed under adverse conditions, the new variety seems to stop growing although retaining its good shape and condition as compared with the earlier variety which continues weak and unsightly growth with elongated pale, small drooping leaves.

My new variety is highly resistant, if not virtually immune to the so-called "shortgun" gunfus, a dehydration problem marring the appearance of the plants.

In addition, my new variety is highly resistant to the disease bacterial soft rot and more resistant than the earlier variety with which it is being compared.

Finally, my new variety may be considered as a medium to large leaved Philodendron, developing and maintaining a compact growth habit longer than known comparable varieties. Its relatively slow rate of growth and compact habit along with its firm, heavy leaf texture, steam and petiole caliper and strength, provides a plant which is very durable and will not stretch or grow rapidly under low light, low humidity and other home and interior conditions.

I have established that my new variety will survive in excess of four weeks under normal home conditions without watering and not wilt, and without apparent damage. My new variety has been asexually reproduced by tip cuttings in the vicinity of Orlando, Fla., and has been found to retain its distinctive characteristics through successive asexual reproduction. The following detailed specification is based on observations made in my greenhouse in Orlando, Fla.

The accompanying drawing, forming a part hereof, shows a typical plant of my new variety, the color being as nearly true as possible with color illustrations of this type. Color references are made to Nickerson Color Fan published by Munsell Color Company, with observations being recorded by daylight illumination under vinyl of not more than 30% shade.

(I) Leaf form characteristics (based on pg. 24, Grafs Exotica 3):

| | |
|---|---|
| (1) Leaf shape: | |
| (a) Mature | Ovate. |
| (b) Immature | Do. |
| (c) Tip | Acute. |
| (d) Base | Cordate. |
| (2) Leaf attachment | Stalked. |
| (3) Leaf arrangement | Alternate. |
| (4) Margin | Entire. |
| (5) Displacement | Smooth. |
| (6) Veination | Pinnate. |
| (7) Lenticels | None. |

(II) Leaf texture characteristics: Firm, thick, leathery, glossy, not prone to crack.

(III) Leaf size characteristics (mature size):

| | Inches |
|---|---|
| (1) Width widest point | 8–8½ |
| (2) Width, 1" from tip | 2–2¼ |
| (3) Length (basal lobe to tip) | 10–11 |

(IV) Leaf petiole length & width (mature size):

| | Inches |
|---|---|
| (1) Petiole length | 6–8 |
| (2) Petiole diameter (measured half the distance stem to leaf) | .35 |

(V) Plant growth characteristics:

(1) Stem caliper (measured 3 nodes down from terminal)—.75″
(2) Distance between internodes (from basal portion each leaf)—¾″–1¼″
(3) Rate of height development—Approximately 75% that of Emerald Queen
(4) Type—Sturdy, dense slow vine (VI) Keeping qualities in homes and other installations: 50% greater than Plant Pat. 3,081.

(VII) Tolerance to bacterial rot: Very resistant.

(VIII) Leaf, stem & petiole color characteristics:

(a) Leaf itself:

(1) Top surface:
(a) Mature ---------- 5GY 6/8
(b) Immature ---------- 7.5GY 6/8
(2) Bottom:
(a) Mature ---------- 5GY 5/6
(b) Immature ---------- 5GY 6/8

(b) Leaf, ribs and veins:
(1) Top:
(a) Mature ---------- 5GY 6/8
(b) Immature ---------- 5GY 8/8
(c) Stem and petiole:
(a) Mature ---------- 5GY 6/8
(b) Immature ---------- 5GY 6/8
(d) Leaf sheen ---------- High gloss

I claim:

1. A new and distinct variety of Philodendron plant substantially as herein disclosed, characterized as to novelty by its density of growth with wide leaves, very short petioles and close internodes, having durability to withstand long periods without watering, appearing to be dormant until watered, the leaves being tough, leathery and very shiny moderate olive green.

No references cited.

ROBERT E. BAGWILL, Primary Examiner